United States Patent
Weaver, II

(10) Patent No.: US 7,364,556 B2
(45) Date of Patent: Apr. 29, 2008

(54) WRIST BRACE HAVING AN ADJUSTABLE THUMB STRAP AND METHOD OF USING SAME

(75) Inventor: Edward L. Weaver, II, Milford, OH (US)

(73) Assignee: Beiersdorf, Inc., Cincinnati, OH (US)

(*) Notice: Subject to any disclaimer, the term of this patent is extended or adjusted under 35 U.S.C. 154(b) by 801 days.

(21) Appl. No.: 10/701,137

(22) Filed: Nov. 4, 2003

(65) Prior Publication Data

US 2005/0096575 A1 May 5, 2005

(51) Int. Cl.
*A61F 5/00* (2006.01)

(52) U.S. Cl. .............................. 602/5; 602/21

(58) Field of Classification Search .................... 602/5, 602/20–23, 64; 2/20, 160, 161.1; 128/877–879
See application file for complete search history.

(56) References Cited

U.S. PATENT DOCUMENTS

| | | | |
|---|---|---|---|
| 3,533,407 A | 10/1970 | Smith | |
| 3,598,408 A | 8/1971 | Klose | |
| 4,047,250 A * | 9/1977 | Norman | 2/161.1 |
| 4,138,108 A | 2/1979 | Robinson | |
| D259,955 S | 7/1981 | Helferich | |
| D270,556 S | 9/1983 | Kneisley | |
| 4,531,241 A | 7/1985 | Berger | |
| 4,584,993 A * | 4/1986 | Nelson | 602/21 |
| D285,821 S | 9/1986 | Kneisley | |
| D288,372 S | 2/1987 | Adams | |
| 4,716,892 A | 1/1988 | Brunswick | |
| 4,854,309 A | 8/1989 | Elsey | |
| 4,883,073 A | 11/1989 | Aziz | |
| D306,364 S | 2/1990 | Hamilton | |
| 5,014,689 A | 5/1991 | Meunchen et al. | |
| 5,160,314 A | 11/1992 | Peters | |
| D339,866 S | 9/1993 | Rice | |

(Continued)

FOREIGN PATENT DOCUMENTS

EP 0 162 610 B1 6/1988

(Continued)

OTHER PUBLICATIONS

PCT Notification of Transmittal of the International Search Report, PCT International Search Report mailed Jun. 28, 2005 for PCT/US2004/036617 (Filed Nov. 3, 2004).

*Primary Examiner*—Michael A. Brown
(74) *Attorney, Agent, or Firm*—Alston & Bird LLP

(57) ABSTRACT

A wrist brace of the present invention for supporting a wrist of the wearer. The wrist brace includes a sheet of flexible material that overlies and supports a wearer's wrist. Defined in the sheet is an opening between a pair of lateral edges, wherein the opening is sized to accommodate a thumb of a wearer. A thumb strap of the wrist brace is defined by a break extending between a distal edge of the sheet of material and the thumb opening. A fastener on one end of the thumb strap allows the thumb strap to be extended between a thumb and index finger so as to secure the wrist brace. Optionally, the thumb opening can have a non-circular shape, such as a triangular shape, with an axis extending in the proximal-distal direction when the wrist brace is worn to promote a better fit around a base of the thumb.

34 Claims, 17 Drawing Sheets

U.S. PATENT DOCUMENTS

| | | |
|---|---|---|
| D340,990 S | 11/1993 | Kawamura |
| 5,313,667 A | 5/1994 | Levine |
| 5,356,371 A | 10/1994 | Hubbard |
| D357,745 S | 4/1995 | Radwell |
| 5,415,624 A | 5/1995 | Williams |
| 5,421,811 A | 6/1995 | More et al. |
| 5,538,501 A | 7/1996 | Caswell |
| 5,566,389 A | 10/1996 | Li |
| 5,695,453 A | 12/1997 | Neal |
| 5,728,059 A | 3/1998 | Wiesemann |
| 5,749,841 A * | 5/1998 | Moore .................. 602/21 |
| 5,759,166 A | 6/1998 | Nelson et al. |
| 5,772,620 A | 6/1998 | Szlema et al. |
| 5,819,313 A | 10/1998 | McCrane |
| D403,425 S | 12/1998 | Taylor et al. |
| 5,873,130 A | 2/1999 | Lafferty |
| 5,928,172 A | 7/1999 | Gaylord |
| 5,987,641 A | 11/1999 | Walker |
| 6,024,714 A | 2/2000 | Katzin |
| 6,024,715 A | 2/2000 | Maxwell |
| D426,640 S | 6/2000 | Bell et al. |
| 6,099,489 A | 8/2000 | Herzberg et al. |
| 6,139,513 A | 10/2000 | Grim et al. |
| 6,142,966 A | 11/2000 | Hely |
| 6,146,348 A | 11/2000 | Slautterback |
| 6,186,969 B1 | 2/2001 | Bell et al. |
| 6,190,344 B1 | 2/2001 | Bobroff |
| 6,191,337 B1 | 2/2001 | Himmelsbach |
| 6,200,286 B1 | 3/2001 | Zamani |
| 6,248,932 B1 | 6/2001 | Himmelsbach |
| 6,261,252 B1 | 7/2001 | Darcey |
| 6,267,743 B1 | 7/2001 | Bodenschatz et al. |
| D456,081 S | 4/2002 | Bell et al. |
| 6,398,748 B1 | 6/2002 | Wilson |
| D461,600 S | 8/2002 | Domanski et al. |
| D461,901 S | 8/2002 | Rodgers |
| 6,561,994 B1 | 5/2003 | Mills et al. |
| D477,088 S | 7/2003 | Brown et al. |
| D477,409 S | 7/2003 | Mills et al. |
| 2002/0193719 A1 | 12/2002 | Yewer |

FOREIGN PATENT DOCUMENTS

| | | |
|---|---|---|
| EP | 0 639 361 A1 | 2/1995 |
| FR | 2 650 176 A1 | 7/1989 |

* cited by examiner

WRIST BRACE HAVING AN ADJUSTABLE THUMB STRAP AND METHOD OF USING SAME

BACKGROUND OF THE INVENTION

1. Field of the Invention

The present invention is related to the field of orthopedic braces, and more particularly, to orthopedic braces for supporting a wrist joint of a wearer.

2. Description of Related Art

Wrist injuries are relatively common orthopedic injuries that occur in a range of environments, such as a home, office or outdoor environment, and can have varying levels of severity. These levels of severity are routinely grouped into two categories, chronic and acute. Acute injuries occur most often due to sudden impacts that involve the large forces caused by an accident or from a collision during athletic activities. Such traumatic injuries to the wrist typically involve broken bones or sprains. Broken bones are usually treated using complete immobilization, while sprains often only require moderate immobilization for a period of weeks depending on the grade of the sprain. Establishing immobilization early after a sprain ensures that the injury does not evolve into a chronic injury.

Repetitive stresses to the wrist joint are the most common cause of chronic injuries. Repetitive stresses often occur in an office environment, e.g., typing, or during labor activities, e.g., assembly line work. Given the range of environments and types of injuries that can occur to the wrist, it is advantageous to have wrist braces that provide a range of flexibility and support for the wearer. In addition, due to the reoccurring, extended duration of chronic wrist injuries, a comfortable wrist brace is also desirable.

U.S. Pat. No. 5,728,059 to Wiesemann et al. ("Wiesemann") discloses a wrist brace 10 including a sheet of flexible material 20 having proximal 26 and distal 28 edges, as well as a pair of opposing lateral edges 30, 40 extending between the proximal and distal edges. Two longitudinally extending pockets 50, 60 are fastened to the sheet 20 and have openings 52, 62 to receive a splint 80. The pockets 50, 60 also include hook or loop type fasteners thereon. Fasteners 46 are attached to the wrist brace 10 along a lateral edge 40 and have complementary hook or loop material thereon, such that the fasteners are capable of attaching to the pockets 50, 60. The Wiesemann patent is also described as being reversible from either the right or left hand (Col. 3, lines 12-15).

The sheet 20 disclosed in the Wiesemann patent is fabricated of flexible and elastic material. With the fasteners being attached to the elastic material, the wearer can adjust the wrist brace to the desired tension and support depending on the amount of immobilization that is required for a wearer's particular injury. Typically, more immobilization would be required for acute injuries, while less immobilization would be required for chronic injuries so that a wearer can still continue with normal activities while the wrist brace is being worn.

As shown in FIGS. 2-3, the Wiesemann patent also discloses that a splint 80 is formed with a curvature to conform to the wearer's wrist and palm, whereby the splint is inserted into either pocket 52, 62 of the wrist brace depending on which hand the wrist brace is to be worn on, and the wrist support is wrapped around the wearer's wrist and hand and secured with fasteners 46. The splint is generally inflexible and provides more immobilization to the wearer's wrist when inserted within the pocket. Thus, the splint would most often be used with acute type injuries, or those chronic injuries where more immobilization is desired.

The various material portions, the fasteners, and the splint provide the versatility to adjust the amount of immobilization depending on the type of injury involved. Wiesemann also discloses a brace that is easy to use given the configuration of the fasteners and flexible material. Despite these improvements, additional innovations in wrist braces to promote better treatment of wrist injuries are also desired.

It would be advantageous to provide a wrist brace that can be adjusted to provide support for a range of injuries, both chronic and acute. In addition, it would be advantageous to have a wrist brace that is easy to use. Finally, it would also be desirable to have a wrist brace that can be used on either a right or left wrist of a wearer.

BRIEF SUMMARY OF THE INVENTION

The present invention addresses the above needs and achieves other advantages by providing a wrist brace of the present invention for supporting a wrist of the wearer. The wrist brace includes a sheet of flexible material that overlies and supports a wearer's wrist. Defined in the sheet is an opening between a pair of lateral edges, wherein the opening is sized to accommodate a thumb of a wearer. A thumb strap of the wrist brace is defined by a break extending between a distal edge of the sheet of material and the thumb opening. A fastener on one end of the thumb strap allows the thumb strap to be extended between a thumb and index finger of the wearer so as to secure the wrist brace. Optionally, the thumb opening can have a non-circular shape, such as a triangular shape, with an axis extending in the proximal-distal direction when the wrist brace is worn to promote a better fit around a base of the thumb.

In one embodiment, the wrist brace of the present invention includes a sheet of flexible material having a distal edge configured to extend at least partially around a hand of a wearer and a proximal edge configured to extend at least partially around a forearm of a wearer. A pair of opposing lateral edges of the sheet of material are configured to at least partially overlap each other so that the sheet of material extends around the wrist of the wearer. A lateral edge fastener is attached at one end to the sheet of material and is configured to extend over one of the lateral edges to attach at another end to the sheet of flexible material. This secures the sheet of material about the wrist.

A thumb opening is defined within the sheet of flexible material between the lateral edges and has a distal thumb opening edge proximate to the distal edge. In addition, a break is defined in the sheet of flexible material and extends between the distal edge of the material and the thumb opening. In this manner, the break, the distal edge, and the distal thumb opening edge define a thumb strap for supporting a thumb strap fastener. The thumb strap is configured to extend between a thumb and an index finger of the wearer, and the thumb strap fastener is configured to extend over the break and attach to the sheet of material so as to enclose the thumb of the wearer within the thumb opening.

Optionally, there may be additional lateral edge fasteners configured to extend over the lateral edge, wherein the lateral edge defines a plurality of radial portions extending inwardly on the sheet of material between the fasteners. The radial portions advantageously reduce bunching. In addition, the lateral edge fasteners may have rounded free ends and flared base ends secured to the sheet of material.

Preferably, the thumb opening defined in the sheet of material is non-circular. For example, the thumb opening may be generally elliptical in shape, wherein a major axis of the generally elliptical shape extends in a proximal-distal direction. As another option, the thumb opening may have a rounded, generally triangular shape. The generally triangular shape may include a base and an apex, wherein the base extends distally and the apex extends proximally to better fit the shape of the base of the wearer's thumb.

Further, the distal edge can be generally parallel to the distal thumb opening edge, such as when both the distal edge of the sheet of material and the distal edge of the thumb opening are distally. The distal edge may also extend continuously between the lateral edges when the fastener is attached to the sheet of flexible material.

Each of the fasteners of the wrist brace may include fastening elements, wherein the sheet of flexible material supports at least one complementary fastening element configured to allow attachment of the fastening elements of the fasteners. The wrist brace may further include two elongated patches of material that support the complementary fastening elements and are attached to the sheet of flexible material. The patches of material may be sufficiently long to extend from the proximal edge to the distal edge of the sheet of flexible material. Further, between the sheet of flexible material and the patches of material may be defined pockets that are sized to receive a splint. In one variation, the fasteners of the lateral edge straps and the thumb strap may attach to the same patch of material. In another variation, the fasteners of the lateral edge straps and the thumb strap may attach to different patches of material.

In yet another aspect, a plurality of undulations may be defined along one of the lateral edges, wherein the lateral edge fastener is attached at a peak of one of the undulations. An additional lateral edge fastener may be attached at an adjacent peak of the undulations so that a radial portion defined by the undulating lateral edge extends between the fasteners.

A wrist brace of another embodiment of the present invention includes a sheet of flexible material. The sheet of flexible material is configured to extend at least partially around a wrist of the wearer. A distal edge of the sheet of material is configured to extend at least partially around a hand of the wearer, while a proximal edge is configured to extend at least partially around an arm of the wearer. A pair of opposing lateral edges define curved portions that extend around a thumb of the wearer when the lateral edges are in a generally adjacent relationship. A pair of thumb straps of the wrist brace are configured to extend between the thumb and an index finger of the wearer. Each of the thumb straps has a first end attached to a respective one of the lateral edges. A top one of the thumb straps has a fastener on its second end and is configured to extend over a bottom one of the thumb straps to attach to the sheet of material using the fastener. Optionally, a second end of the bottom one of the thumb straps may be attached to the sheet of material near the first end of the top one of the thumb straps.

The wrist brace of the present invention has many advantages. The thumb hole allows insertion of the wearer's thumb and facilitates proper positioning before securing the sheet of material the wearer's wrist. This is done by avoiding the difficulty of trying to hold the sheet of material in place while at the same time trying to overlap the lateral edges and fix the fasteners in place. The non-circular shape of the thumb opening also promotes positioning and improved fit by having its long axis oriented in the proximal-distal direction where the base of the thumb is typically widest. The rounded triangular shape allows for a broader opening at the base of the thumb for a further improved fit.

The ability of the thumb strap to be removed and reattached via the fastener allows readjustment for maximum fit and comfort. Thus, the thumb strap and thumb hole act to position and secure the brace about a wearer's wrist. The break in the sheet of material ensures that when reattached, the thumb strap allows for a continuous distal edge of the sheet of material. The radial portions reduce bunching between the fasteners when attached to the sheet of material. In addition, the fasteners have a rounded free end, as well as a flared end attached to the lateral edge, thereby reducing catching on articles of clothing while at the same time facilitating better attachment. The configuration of the fasteners and elongated strips enables the fasteners to be positioned for securing the wrist brace when on either the wearer's right or left wrist.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Figure 1:
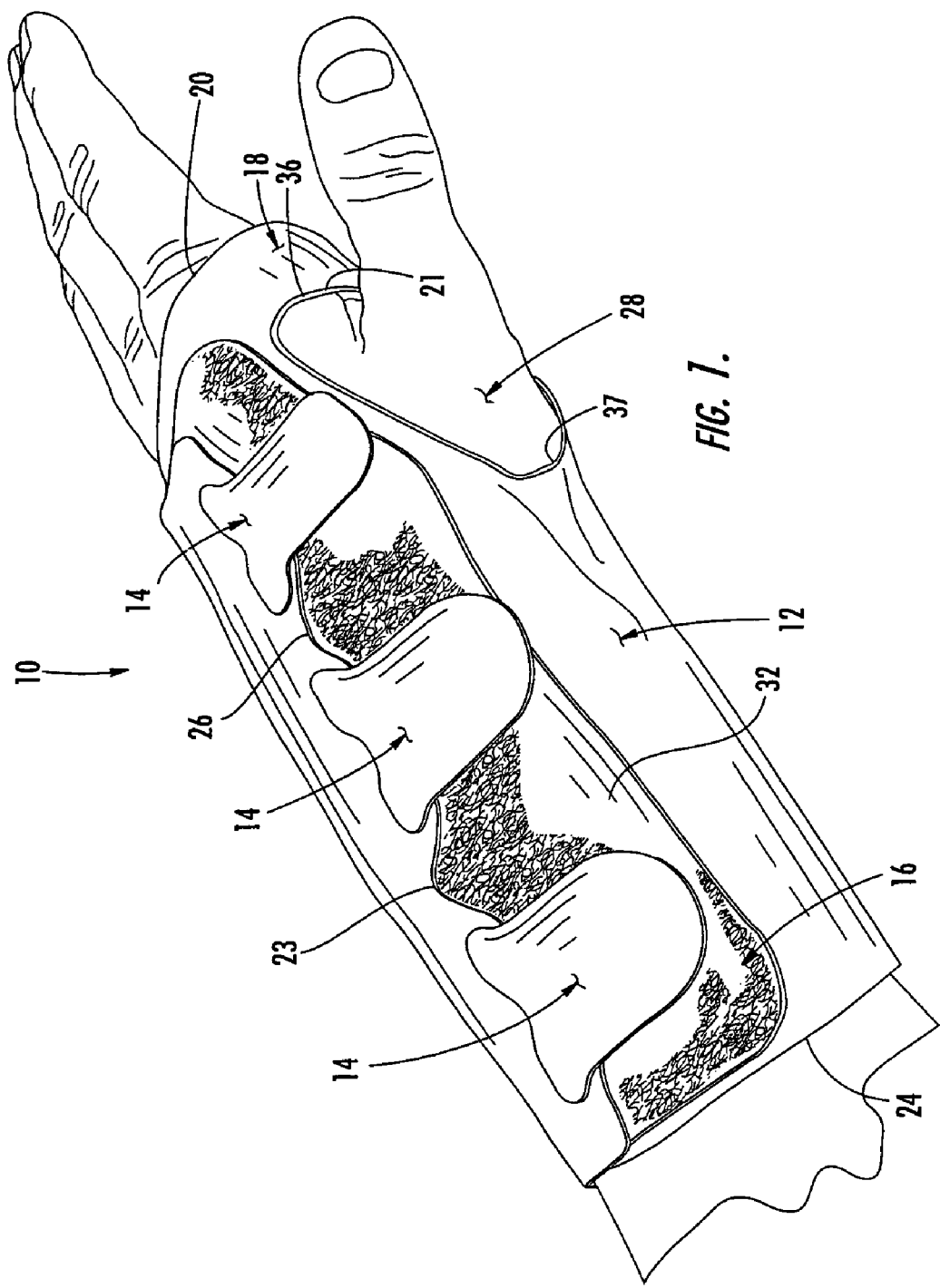
FIG. 1 is a perspective view of a wrist brace of one embodiment of the present invention on a left hand.
Figure 2:
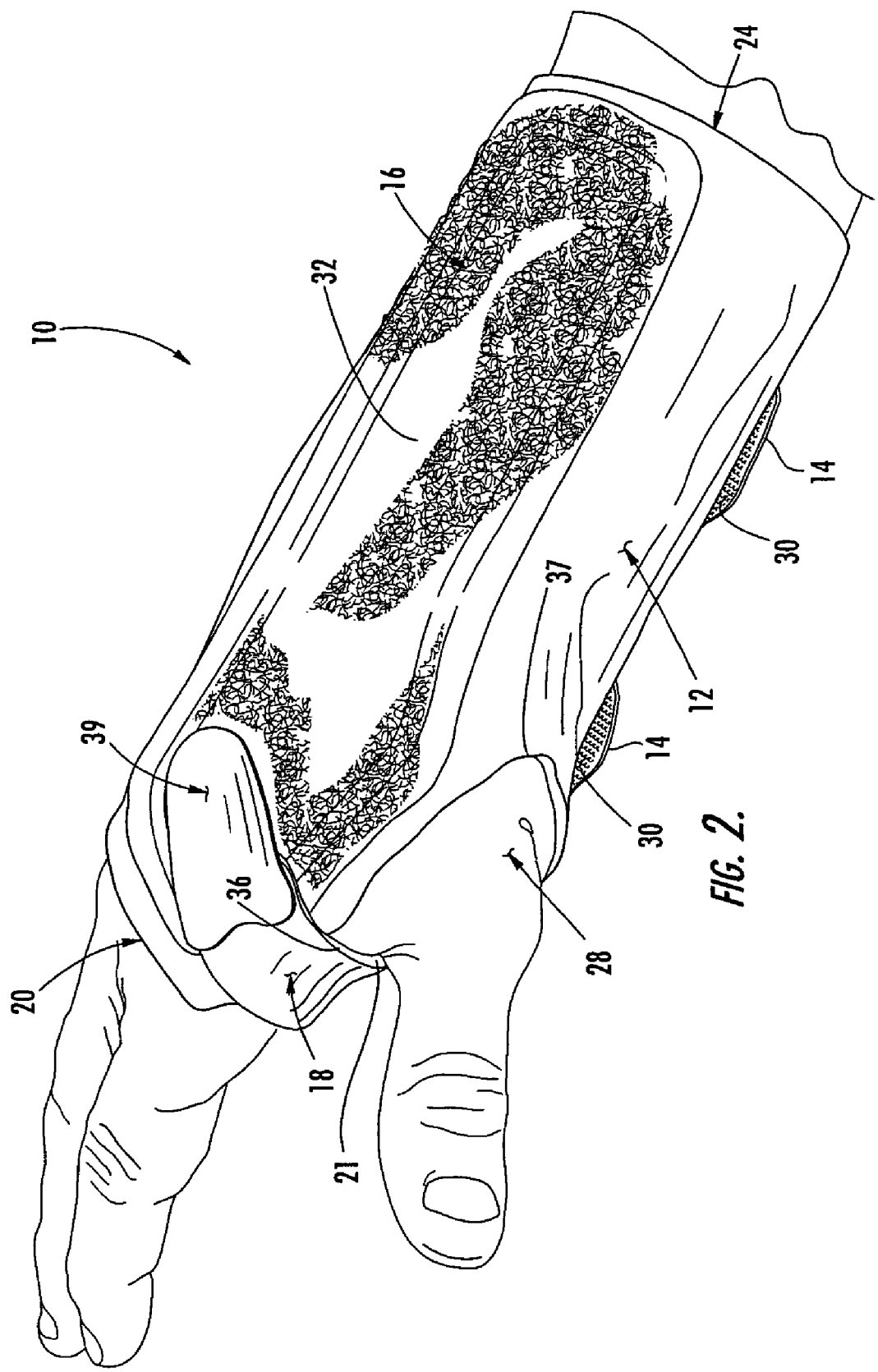
FIG. 2 is another perspective view of the wrist brace shown in FIG. 1 on a right hand.

Generally, a wrist brace 10 of the present invention includes a sheet of material 12 for extending around, and supporting, a wrist of a wearer, a plurality of fasteners 14 for securing the sheet of material about the wrist and a thumb strap 18 for extending between a thumb and index finger of the wearer so as to further secure the wrist brace, as is shown, for example, in FIGS. 1 and 2.

Figure 3:
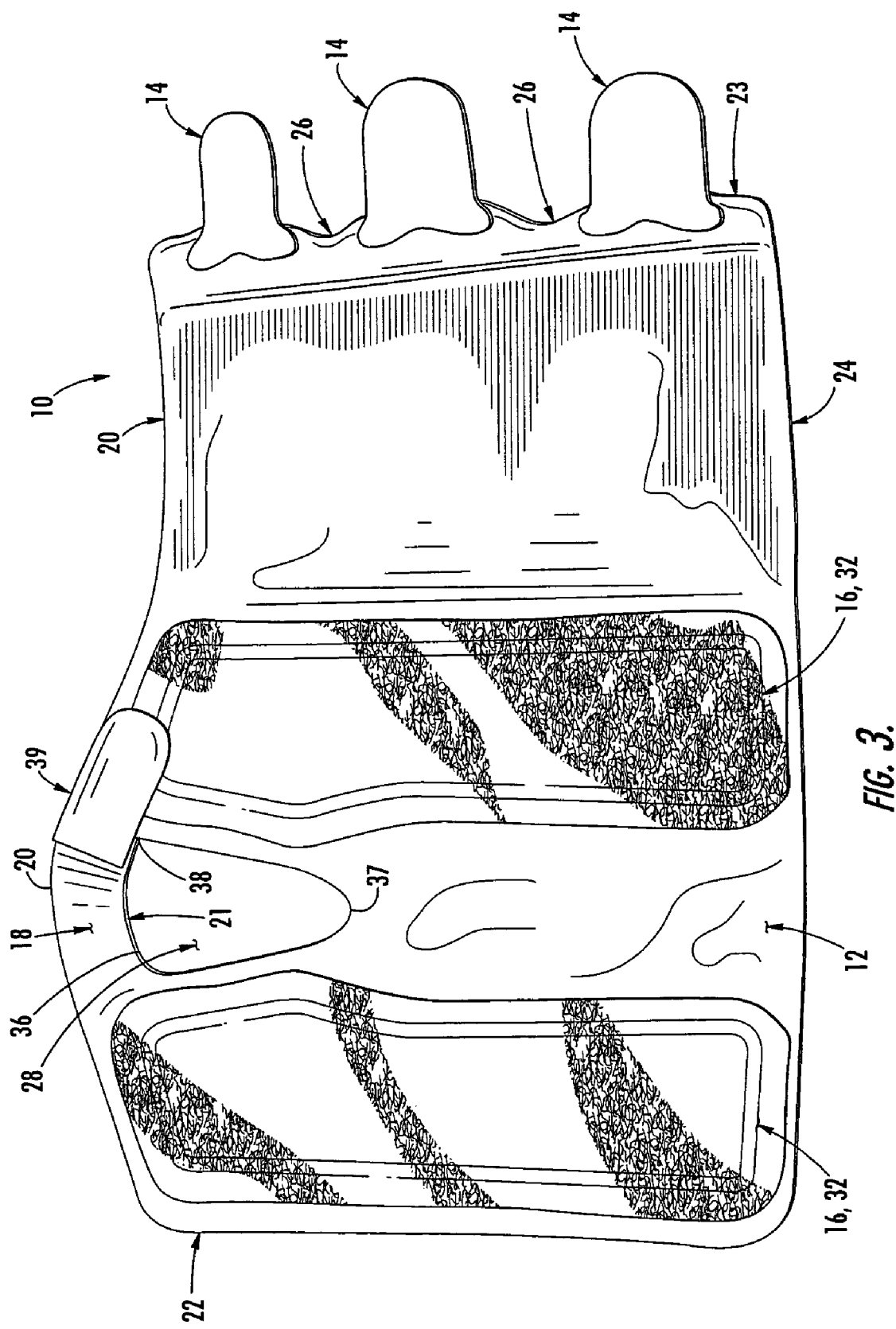
FIG. 3 is a plan view of an outer surface of the wrist brace shown in FIG. 1.
Figure 6:
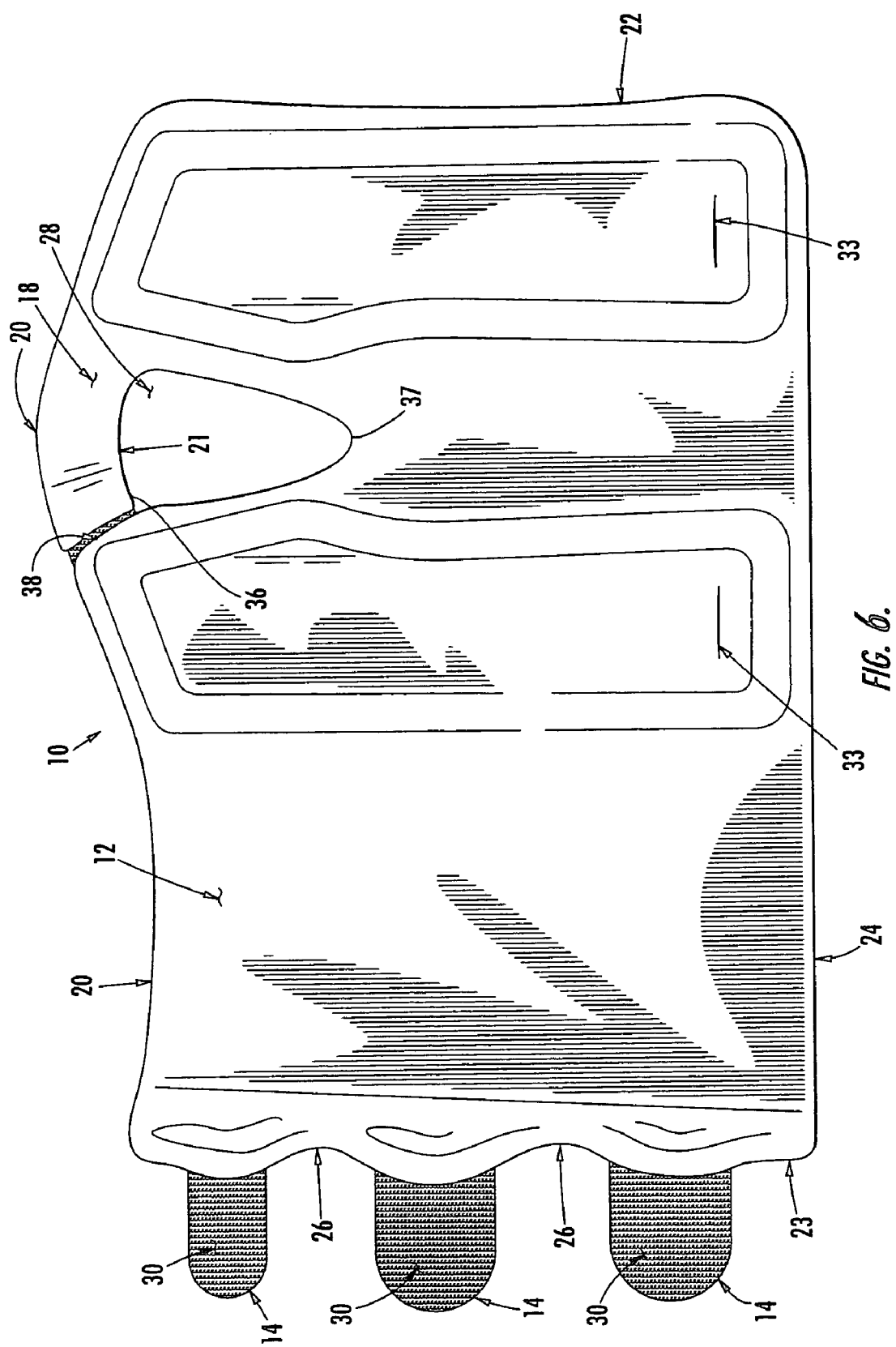
FIG. 6 is a plan view of an inner surface of the wrist brace shown in FIG. 1.

In one embodiment of the present invention, the sheet of material 12 has lateral edges 22, 23, distal edge 20, and proximal edge 24, as is shown in FIG. 3. The lateral edges are spaced from each other across the body of the sheet of material 12 and, in the illustrated embodiment of FIG. 3, are generally straight and approximately parallel to each other. However, lateral edge 23 can have an undulating shape (as shown in FIG. 6) with peaks that correspond to attachment of the fasteners 14, as will be described in more detail below.

The distal edge 20, so defined due to its more distal anatomical position on the wrist when worn, has a more varied shape than the relatively straight lateral edges with an outwardly curved portion adjacent the thumb strap 18 to facilitate accommodation of the thumb of the wearer. The proximal edge 24 (again defined by its relative anatomical position when worn) is relatively straight and parallel to the more linear portions of the distal edge 20.

When the wrist brace 10 is applied to a wearer's wrist, the distal edge 20 extends around the wearer's hand, the proximal edge 24 extends around the wearer's forearm, and one of the opposing lateral edges 23 overlaps the other one of the lateral edges 22 to extend around the wrist of the wearer, as illustrated in FIGS. 1-2. Overlapping the lateral edges, therefore, results in a generally cylindrical tube which extends over the hand, wrist and forearm of the wearer.

The sheet 12 of flexible material is preferably constructed of a laminate material, wherein there is at least one fabric moisture wicking layer adjacent to the skin and the fabric moisture wicking layer is bonded to a polyurethane foam layer. Alternatively, two fabric layers may be bonded on opposite surfaces of the polyurethane layer. In addition, the moisture wicking layer may be an engineered fabric, or chemically treated, to provide moisture wicking properties.

It should be noted that the sheet of flexible material 12 could include any number or combination of elastic or inelastic materials, as long as it is capable of conforming to, and providing support for, the wrist of the wearer. Although the illustrated embodiment shows the sheet of material 12 as having distal 20, proximal 24, and lateral edges 22, 23 in a generally rectangular shape, the sheet of material of the present invention should not be considered limited to any particular number of edges with any particular shape. For example, the sheet 12 of flexible material could have a circular shape wherein the edges 20, 22, 23 and 24 are arc portions of an outer circular edge and are still capable of extending at least partially around the hand and forearm of a wearer and encircling the wrist of the wearer.

Figure 7:
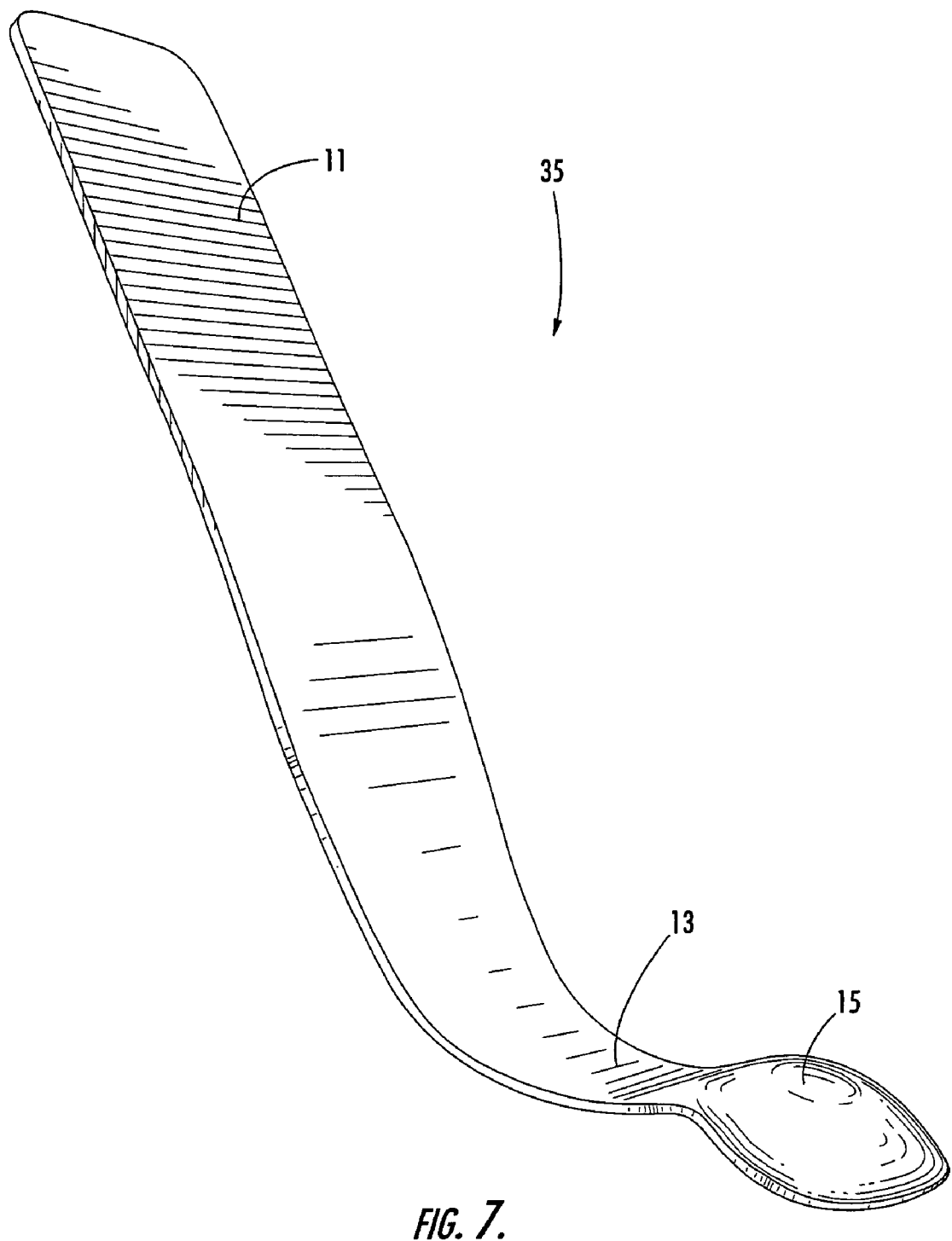
FIG. 7 is a perspective view of a splint used with the wrist brace shown in FIG. 1.

Optionally, the wrist brace 10 may include two patches of material 32 attached to a surface of the sheet of material 12 and defining pockets between the patches and the sheet of material, as shown, for example, in FIG. 3. The proximal-distal, and lateral, dimensions of the patches 32 are such that the pocket extends substantially from the proximal edge 24 of the sheet of flexible material 12 to the distal edge 20 of the sheet of flexible material. These dimensions preferably allow an elongated splint 35 (as shown in FIG. 7) to be accommodated alternatively in one of the pockets defined under each of the patches of material 32. Together, the pocket and splint provide further support for the wearer's wrist and hand, as will be described in more detail hereinbelow.

Advantageously, use of two patches of material 32 to define two pockets in different locations allows the splint 35 to be switched for left and right handedness, as shown in the illustrated embodiments. However, a single one of the patches of material 32 may be employed for a wrist brace having only a single handed orientation.

As yet another option, a wrist brace of the present invention more directed to flexible support of a chronically injured wrist may not employ the splint 35 at all, making the patches of material 32 unnecessary, at least to the extent that they define pockets. This would most often be the case with chronic type injuries wherein greater freedom of motion may be desirable to allow for more wrist movement. As will be described in more detail below, each of the patches of material 32 may also support, or act as, a fastening element (e.g., loop material, one-half of a snap, etc.) that is complementary to and allows attachment of the fasteners 14.

The wrist brace 10 may also include slits 33 defined in the sheet of material 12 on the opposite side of the sheet from the patches of material 32, as shown in FIG. 6. The slits 33 allow for insertion of the splint 35 within the pocket defined by the patch of material 32. Additionally, the slits 33 permit removal and exchange of the splint 35 to the pocket defined by the other one of the patches of material 32 when the wrist brace 10 is used on an opposite hand. Alternatively, the slits 33 could also be defined directly in the patches of material 32.

The splint 35 for insertion into one of the pockets defined by the patches of material 32 has an elongate shape that includes a planar portion 11, an arc portion 13 and a crown portion 15, as is shown in FIG. 7. The preferred splint 35 of the illustrated embodiments is shaped from an elongate, rectangular sheet of rigid material (e.g., aluminum) using a stamping process. The planar portion 11 comprises about half of the length of the splint 35 and generally retains the original, unstamped shape of the sheet of material. The arc portion 13 extends away from the plane of the planar portion in an arc between the planar portion 11 and the crown portion 15. The crown portion has a slightly convex curvature and extends away from the arc portion at an angle more oriented in parallel with the planar portion 11.

The longitudinal and lateral dimensions of the splint 35 are such that the splint extends substantially from the proximal edge 24 to the distal edge 20 under one of the patches of material 32. When the splint 35 is positioned within one of the pockets defined by the patches of material 32, the crown and arc portions 15, 13 align with the wearer's palm and wrist, respectively, to maintain the wearer's hand in extension relative to the wrist. The planar portion 11 extends along the wearer's forearm. Such a position is typically considered anatomically neutral so as to reduce strain on the wrist.

It should be noted that if employed, the splint 35 could have any number of shapes, sizes and materials (steel, wood, plastic, etc.) so as to accommodate different wrist sizes, as well as to adjust the desired amount of immobilization. For instance, the splint could be planar along its length, as opposed to the shaped splint of the illustrated embodiments.

The plurality of fasteners 14 are spaced apart from each other along one of the lateral edges, such as the lateral edge 23 of the embodiment illustrated in FIG. 3. In particular, a first fastener is located near the distal edge 20, a second fastener is located near the proximal edge 24, and a third fastener is located between the first and second fasteners. The fasteners 14 support fastening elements 30 and each include a base end attached to the sheet of material 12, as shown in FIG. 3, and a free end extending therefrom over the lateral edge 23. Preferably, the base end of each of the fasteners 14 is attached adjacent the lateral edge 23 of the sheet using radio frequency (RF) welding, stitching, adhesive, or similar techniques, that provide a robust connection for repeated attachment, removal and reattachment of the fastening elements 30 supported by their free ends.

In the various embodiments illustrated herein, the wrist brace 10 is shown as having two or three fasteners 14. However, the wrist brace 10 of the present invention could have one or more fasteners 14 depending upon the desired fit, and security, of the sheet of material 12 around the wrist of the wearer. Therefore, various numbers of fasteners may be employed and still be within the scope of the present invention. The sheet of material may also be shaped as a continuous tubular sleeve, and in which case no fasteners 14 are required.

Preferably the fasteners 14 are constructed of a flexible and stretchable material allowing them to conform to the shape of the sheet of material 12. However, the fasteners 14 may also be constructed of non-stretchable and non-flexible materials, especially if the sheet of material 12 is capable of conforming to the fasteners at their attachment locations. In addition, the fasteners 14 preferably have a width, height, or other combination of dimensions, that provide a surface area sufficiently large enough to accommodate the fastening elements 30.

An outer surface of the patches of material 32 each support fastening elements 16 that are complementary to the fastening elements 30 supported by the fasteners 14. In this manner, fastening elements 16 extend substantially from the proximal edge 24 of the sheet of material 12 to the distal edge 20 of the sheet of material, as shown in FIG. 3.

Preferably, the fastening elements 30 located on an outer surface of the fasteners 14, as well as the fastening elements 16 located on the patches of material 32, are constructed of a complementary hook and loop material such as VELCRO®. However, the term "fastening element" as used herein denotes any type of chemical, mechanical or other fastener that allows connection of two separate components, such as snaps, hook and loop connectors, adhesives, snaps, buckles, etc. Notably, the fastening elements 30 (hooks) located on the outer surface of the fasteners 14 and the fastening elements 16 (loops) located on the patches of material 32 mate to and attach with one another when brought into contact. These fastening elements, therefore, are referred to herein as being complementary.

Figure 4:
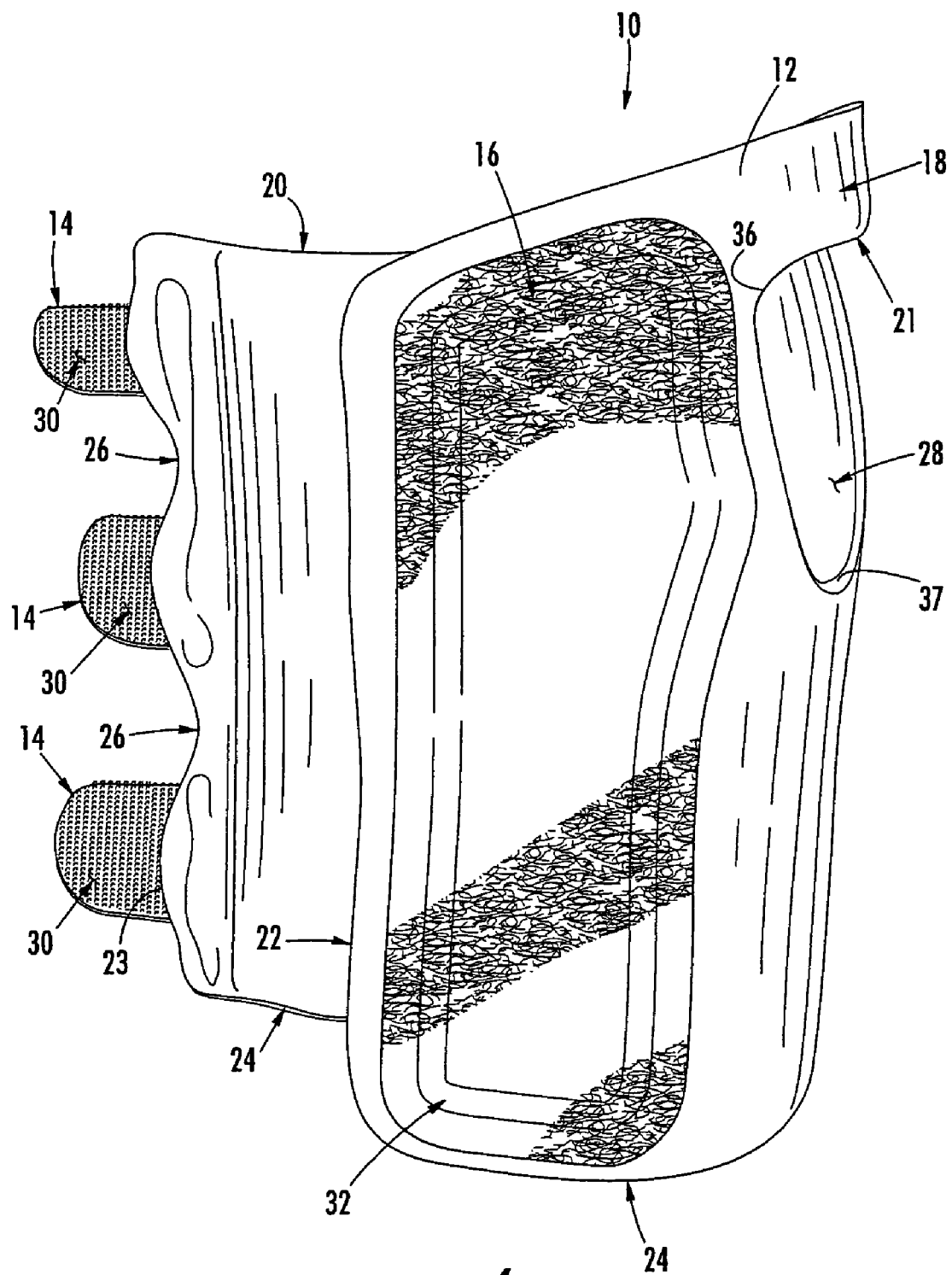
FIG. 4 is another perspective view of the wrist brace shown in FIG. 1.

As another option, which was briefly mentioned above, the lateral edge 23 may include a plurality of undulations wherein each of the fasteners 14 is attached adjacent to, and extends over, one of the peaks, as is shown in FIG. 4. Between the fasteners 14 and peaks are defined radial portions 26 extending inwardly between the fasteners. The radial portions 26 facilitate stretching of the sheet of material 12 along the lateral edge 23 and adjacent to the fasteners 14 (i.e., the peaks) during attachment of the fasteners. Additionally, the radial portions 26 allow attachment of the fasteners 14 with a minimum of bunching of the sheet of material 12 at the lateral edge 23. In general, the radial portions 26 preferably have a radius of about ½ of an inch, but could range between ¼ to 1 inch.

Figure 5:
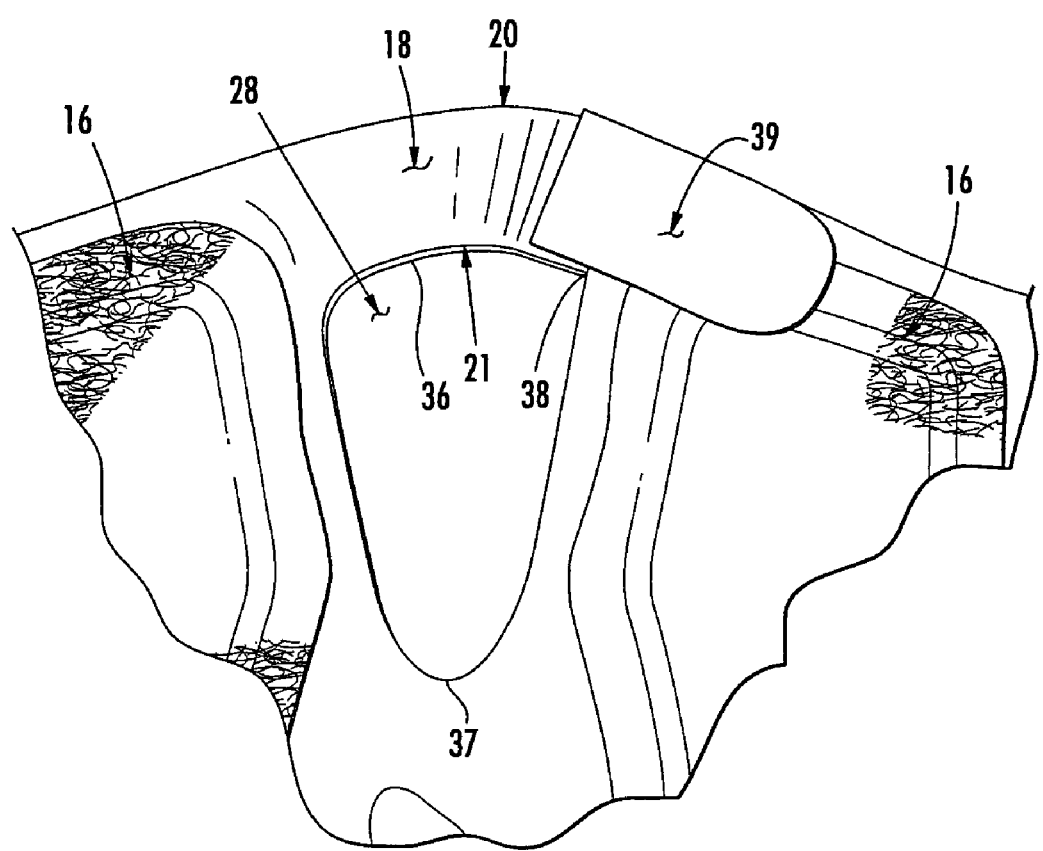
FIG. 5 is an enlarged view of a fastening strap of the wrist brace shown in FIG. 1.
Figure 10:
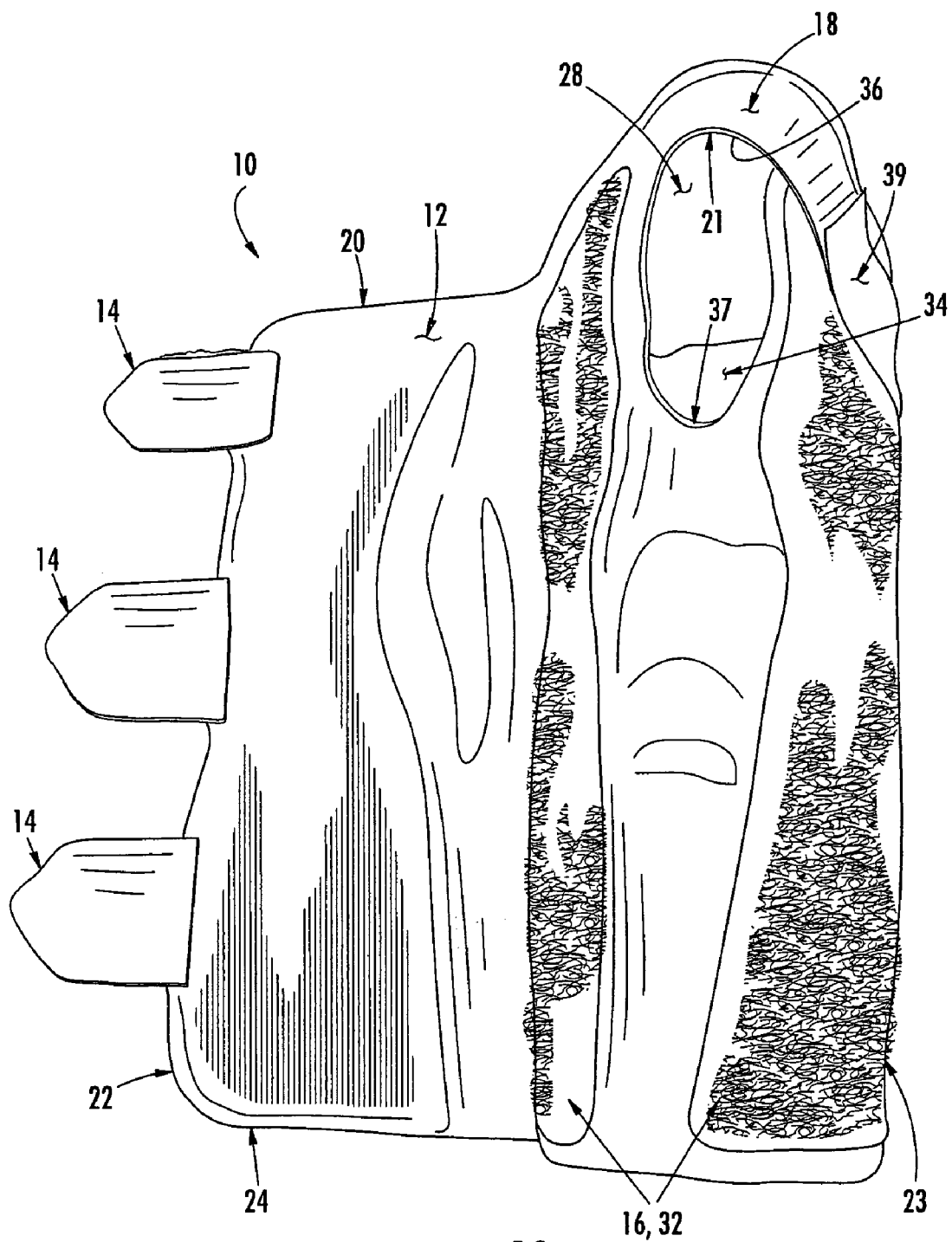
FIG. 10 is a plan view of an outer surface of the wrist brace shown in FIG. 8.

Defined within the sheet of material 12 between the lateral edges 22, 23 and adjacent the distal edge 20 is a thumb hole 28 for accommodating a thumb of the wearer, as shown in FIG. 5. Preferably, the thumb hole has a generally non-circular shape that provides a better fit at the base of the wearer's thumb. For example, the thumb hole 28 could be generally elliptical, wherein a major axis of the generally elliptical shape extends in a proximal-distal direction, as shown in FIG. 10. In another example, the thumb hole 28 could be generally triangular in shape having a base 36 and an apex 37, as shown in FIGS. 3 and 5. When the wrist brace 10 is worn, the base extends in the distal direction so as to be positioned between the wearer's thumb and forefinger.

Although the illustrated embodiments include two examples of non-circular shaped openings for the thumb hole 28 (i.e., the elliptical and triangular openings), other non-circular shaped openings could be employed depending on the desired fit around the base of the wearer's thumb, such as rectangular or square openings with rounded edges.

Partially defining the thumb hole 28 is a distal thumb opening edge 21 that is in proximity to the distal edge 20 of the sheet of material 12. Optionally, the distal thumb opening edge 21 may parallel the distal edge 20. For example, the distal thumb opening edge 21 arcs distally to trace the distally arcing shape of the distal edge 20 of the embodiment illustrated in FIGS. 5 and 6.

Regardless of the shape and relative positions of the distal thumb opening edge 21 and distal edge 20, these two edges, along with a break 38 in the sheet of material 12 extending between the edges 20, 21 can define the thumb strap 18. A fastener 39 supporting its own fastening element (such as the hook material described above) is attached to one free end of the thumb strap and is sufficiently long to extend over the break 38 onto the complementary fastening element supported by the adjacent one of the patches of material 32 on the sheet of material 12, as illustrated in FIG. 5.

Similar to the fasteners 14 described above, the fastener 39 could be attached to the thumb strap 18 in several ways and still be within the scope of the present invention. Preferably the fastener 39 on the thumb strap 18 is attached using radio frequency (RF) welding so that no stitching is required. However, adhesives, stitching, staples, combinations thereof, or other methods and fixation devices could be used to secure the fastener 39 onto the free end of the thumb strap 18.

Advantageously, definition of the thumb strap 18 via the break 38 in the sheet of material 12 allows the free end of the thumb strap (because it has the same thickness and width) to tightly abut the rest of the sheet of material when the fastener 39 is attached to the patch of material 32. In this manner, the distal edge 20 of the sheet of material extends continuously between the lateral edges 22, 23 when the thumb strap is closed about the thumb of the wearer, as is shown in FIG. 6. Also advantageously, the fastener 39 may have generally the same width and extend at the same angle as the free end of the thumb strap so as extend smoothly along the distal edge 20 of the sheet of material 12, as shown in FIG. 5.

Dimensionally, the thumb strap 18 is preferably configured to fit between the thumb and the index finger of the wearer. In addition, the thumb hole 28 is preferably capable of accommodating a wide range of thumb sizes. Generally, to fit a wide range of hand sizes, the thumb strap 18 can have a width of ¾ of an inch, but may also be within the range of ½ to 1½ inches in width. In addition, the thumb hole 28 preferably has a length of approximately 2¾ inches from its apex 37 to the center of the distal thumb opening edge 21, and a length of about 1¼ inches along the distal thumb opening edge. The apex to distal opening edge could also range from about 1½ to 3 inches, and the distal thumb opening edge from ¾ to 2 inches depending upon the size of the wearer and the desired tightness of fit.

During use, the wrist brace 10 is manipulated from an open position, such as is shown in FIG. 3, to being secured on the hand, wrist and forearm of a wearer as shown in FIGS. 1 and 2. Preferably, the fastener 39 of the thumb strap 18 (if open) is attached via respective complementary fastening elements 16, 30 to the one of the patches of material 32 adjacent to the thumb hole 28 so as to close off the thumb hole. The wearer then inserts the thumb of one hand through the thumb hole 28 until the non-circular opening has its major axis oriented in the proximal-distal direction at the base of the thumb. In this manner, the thumb strap 18 extends between the thumb and index finger of the wearer.

While supported from the thumb, the lateral edge 23 of the sheet of material 12 is extended over the other lateral edge 22 and around the wearer's arm and wrist. The remaining fasteners 14 are then extended over the lateral edge 23 and attached to the other one of the patches of material 32. Advantageously, attachment to different patches of material 32 by the fasteners 14 along the lateral edge 23 avoids overlap or conflict between the lateral edge fasteners and the fastener 39 at the end of the thumb strap 18.

Notably, the anatomical position of the fasteners 14 is switched when switching between a left handed (FIG. 1) to a right handed (FIG. 2) orientation. In particular, the thumb strap 18 fastens to the palmar side of the wrist brace 10 when the brace is worn on the wearer's left hand, as shown in FIG. 1. Also, the remaining fasteners 14 extending from the lateral edge 14 attach on the dorsal surface of the arm. However, when the brace 10 is worn on the wearer's right hand, the thumb strap 18 attaches to the dorsal surface of the hand and the remaining fasteners 14 attach to the volar surface of the forearm, as shown in FIG. 2.

Optionally, for additional support, the splint 35 can then be inserted into the pocket defined between the sheet of material 12 and one of the patches of material 32 positioned adjacent the volar and palmar side of the wrist and hand. For instance, the splint 35 can be inserted through the slit 33 in the sheet of material 12 underlying the patch of material near the proximal edge 24, as shown in FIG. 6. Thus, if the brace 10 is worn on the right hand, the splint 35 would be inserted into the pocket closest to the lateral edge 22. If the brace 10 is worn on the left hand, the splint 35 is inserted into the other pocket.

Figure 8:
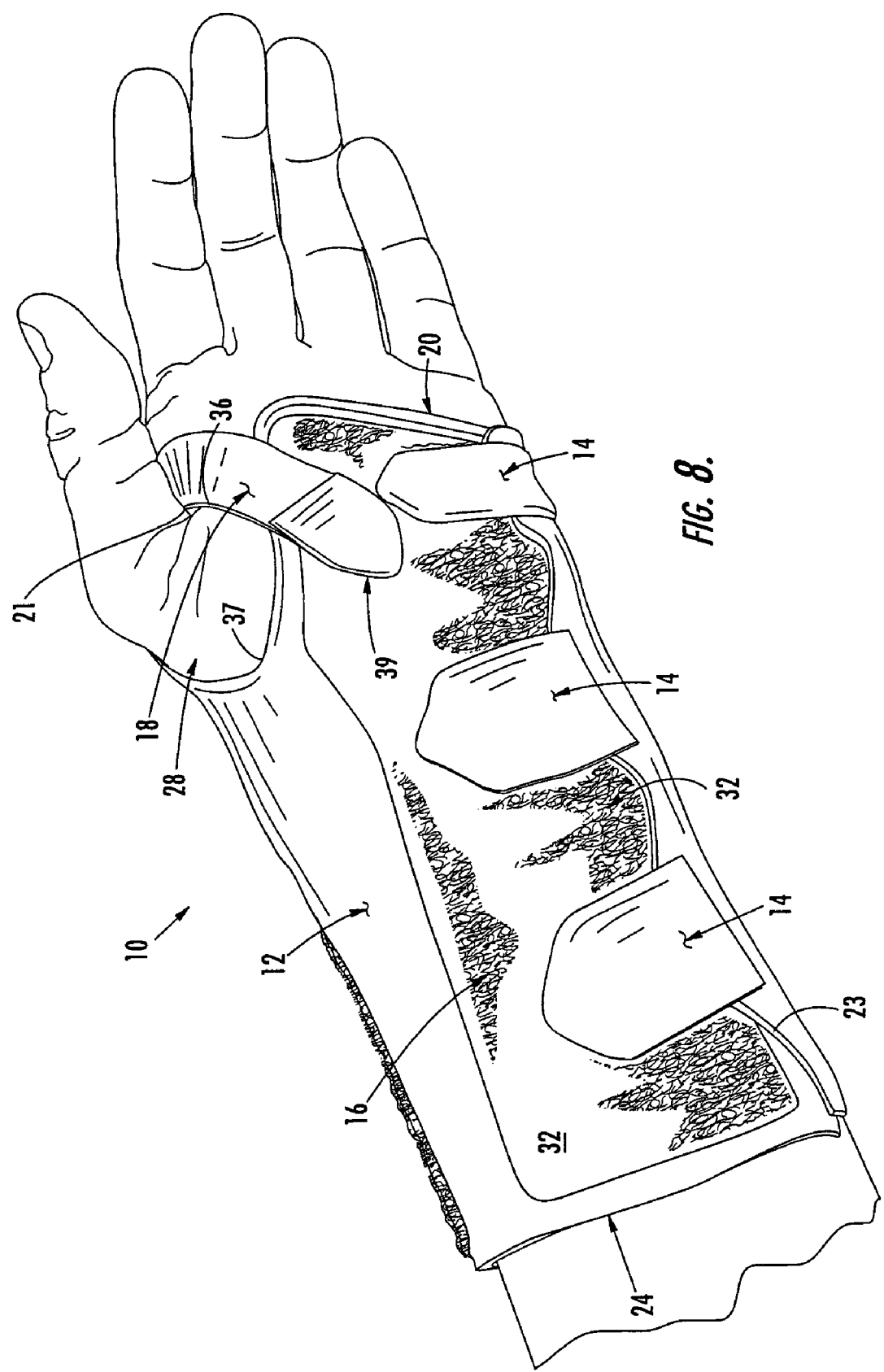
FIG. 8 is a perspective view of a wrist brace of another embodiment of the present invention on a left hand.
Figure 9:
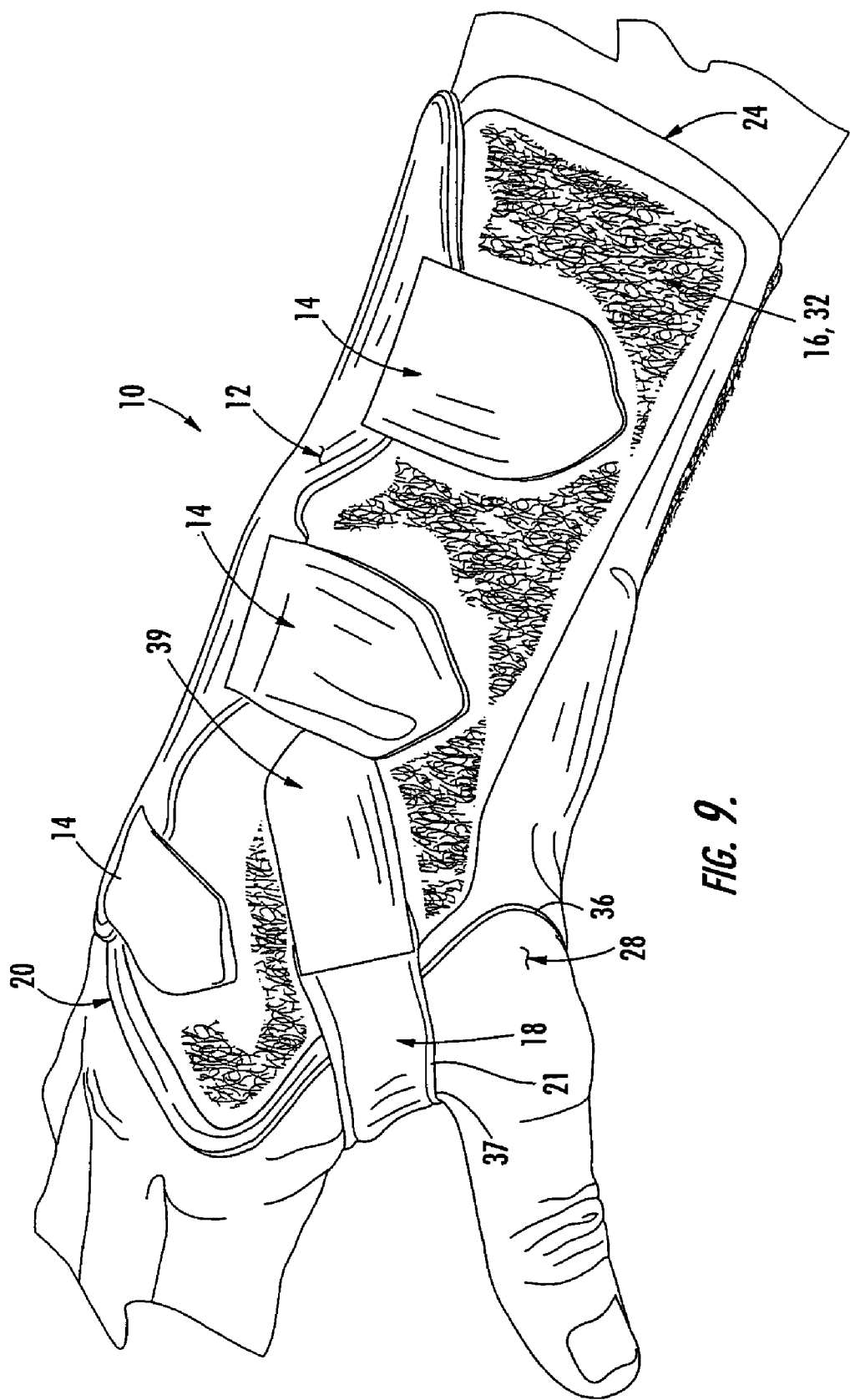
FIG. 9 is a perspective view of the wrist brace shown in FIG. 8 on a right hand.
Figure 11:
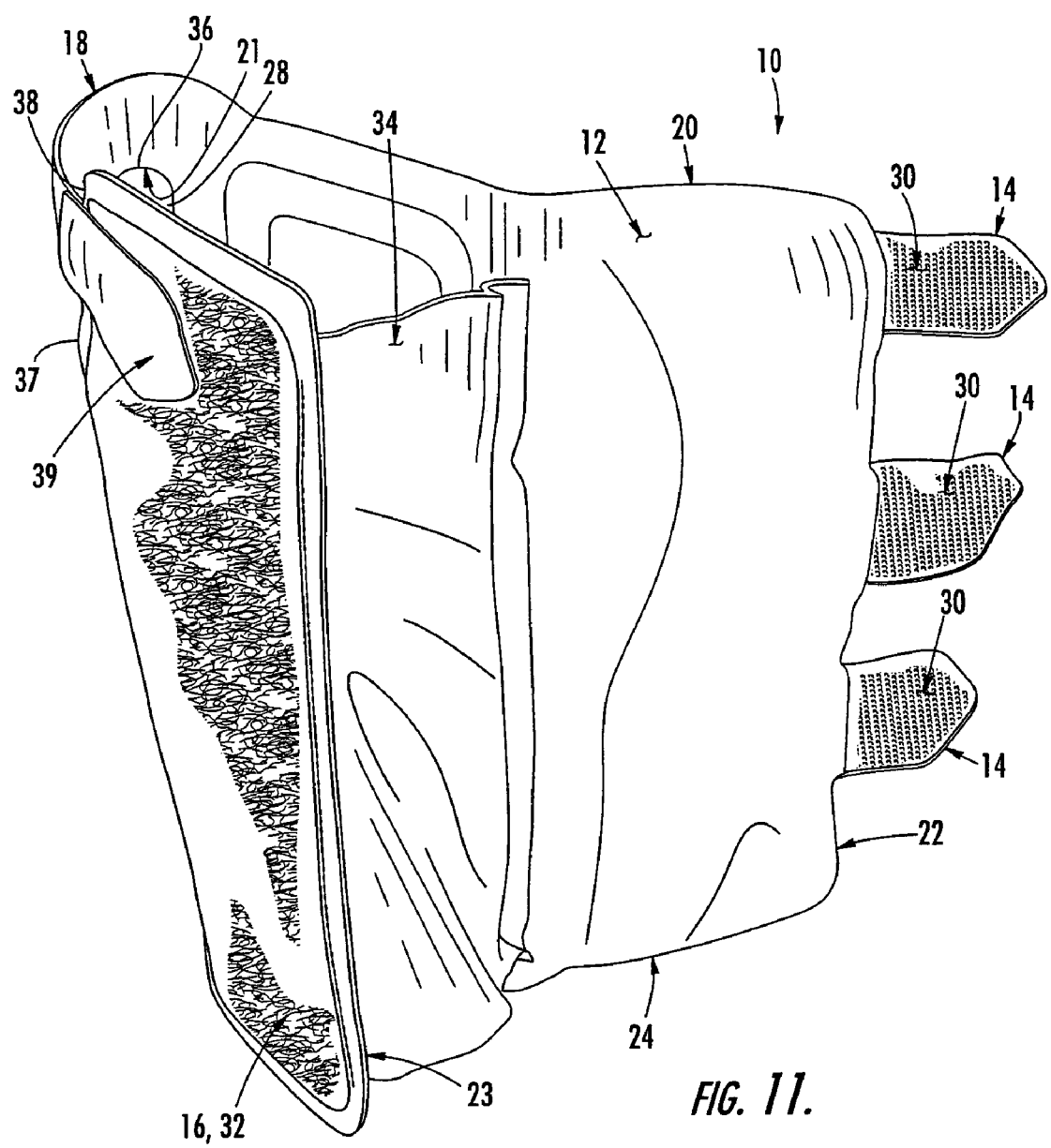
FIG. 11 is a perspective view of the wrist brace shown in FIG. 8.

Another embodiment of the wrist brace 10 of the present invention is shown in FIGS. 8-11. In this embodiment, the fasteners 14 are located along the lateral edge 22 instead of the lateral edge 23, as shown in FIGS. 10 and 11. As a result, all of the lateral edge fasteners 14, as well as the fastener 39 on the thumb strap will attach to the same fastening element 16 on either the palmar side for the right hand, as shown in FIG. 8, or the volar side for the left hand, as shown in FIG. 9.

In addition, the wrist brace 10 may also include a sleeve 34 that is attached to an inner surface of the sheet 12, as shown in FIG. 11. The sleeve 34 is generally used to facilitate holding the sheet of material 12 to the wearer's wrist during attachment of the fasteners 14. Similar to the sheet of material 12, the sleeve may be constructed of a range of materials, including moisture wicking materials and elastic materials.

Figure 12:
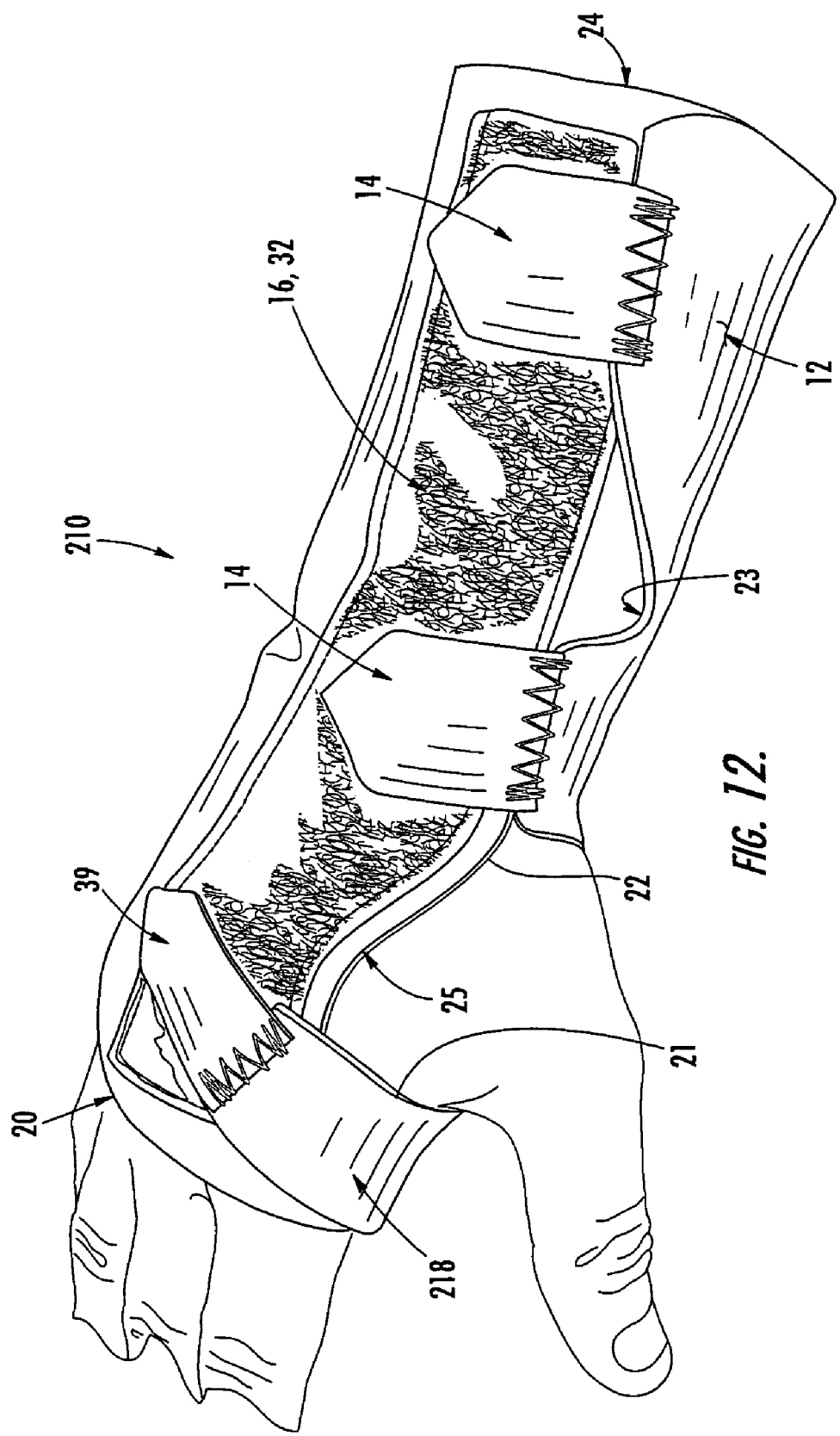
FIG. 12 is a perspective view of a wrist brace of yet another embodiment of the present invention on a right hand.
Figure 13:
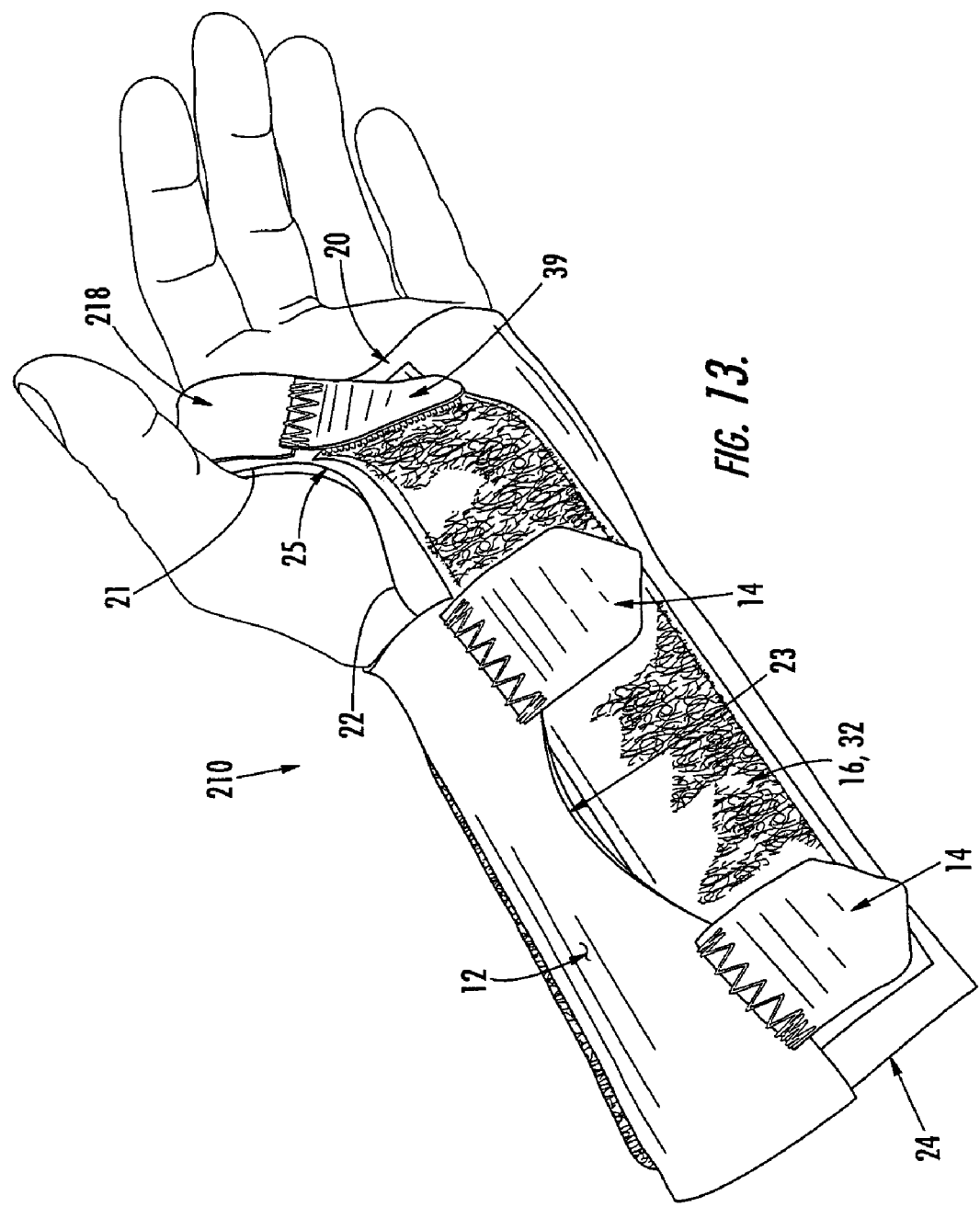
FIG. 13 is a perspective view of the wrist brace shown in FIG. 12 on a left hand.
Figure 14:
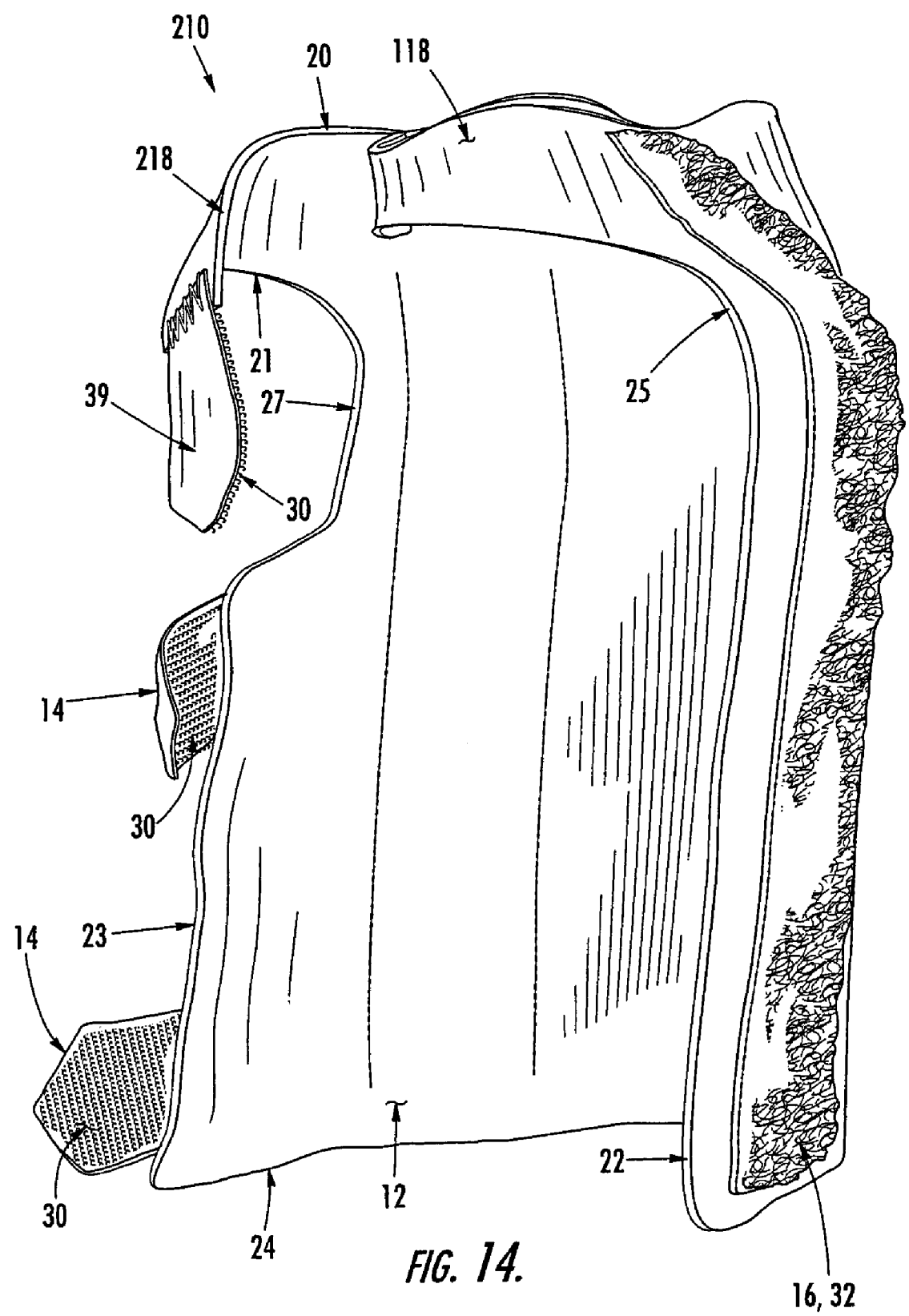
FIG. 14 is another perspective view of the wrist brace shown in FIG. 12.
Figure 15:
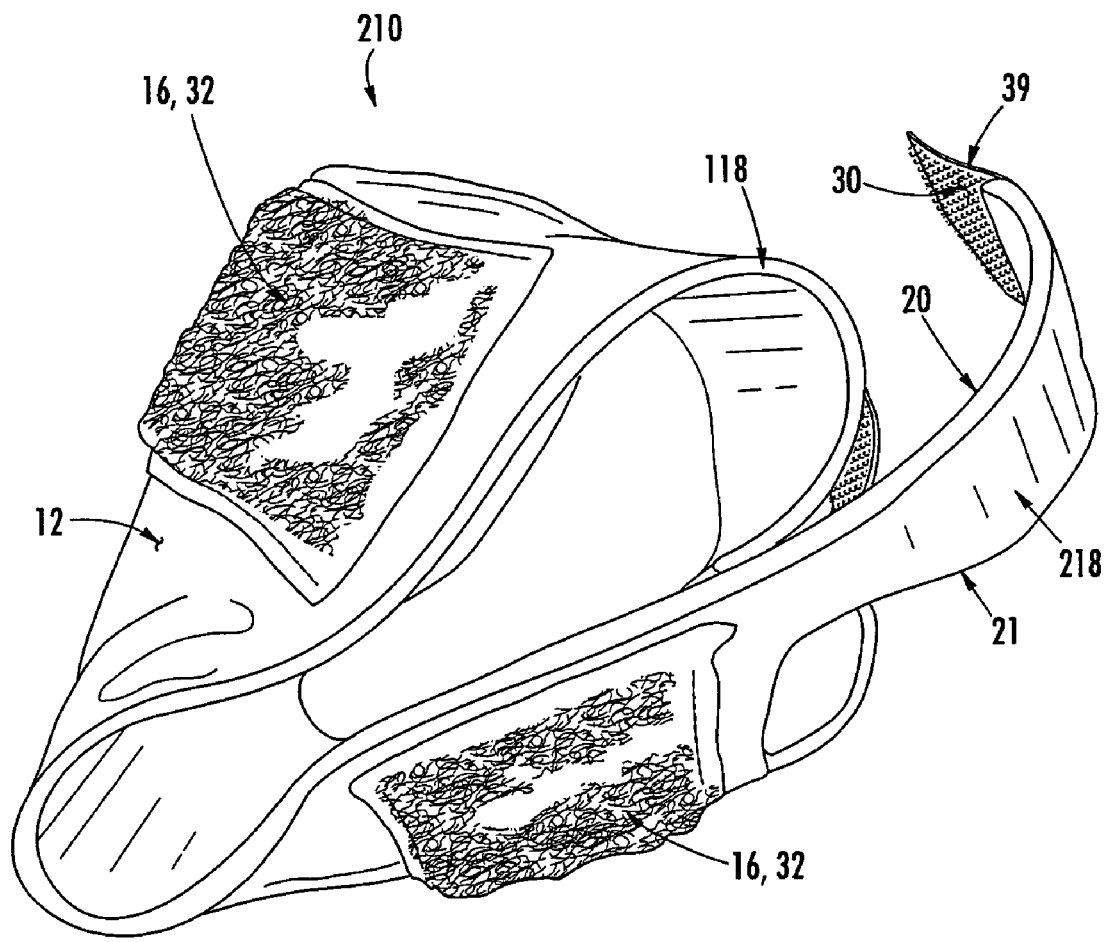
FIG. 15 is a side elevation view of the wrist brace of FIG. 12.

In another embodiment of the wrist brace 10 of the present invention, the lateral edges 22, 23 include curved portions 25, 27 that are configured to extend around the base of the thumb when the wrist brace is wrapped around the wrist of a wearer, as shown in FIGS. 12-14.

In addition, a pair of opposing thumb straps 118, 218 extend from the lateral edges 22, 23. A bottom one of the thumb straps 118 extends from and is integrally part of the lateral edge 23 of the sheet of material 12 and attaches at the base of the other, top one of the thumb straps 218. Thumb strap 218 is also integrally formed with the sheet of material 12, extends from the other lateral edge 22 and includes the fastener 39 supported on its free end, as shown in FIGS. 12 and 13. In this manner, the pair of thumb straps 118, 218 can overlap each other as they extend between the thumb and index finger of the wearer.

Figure 16:
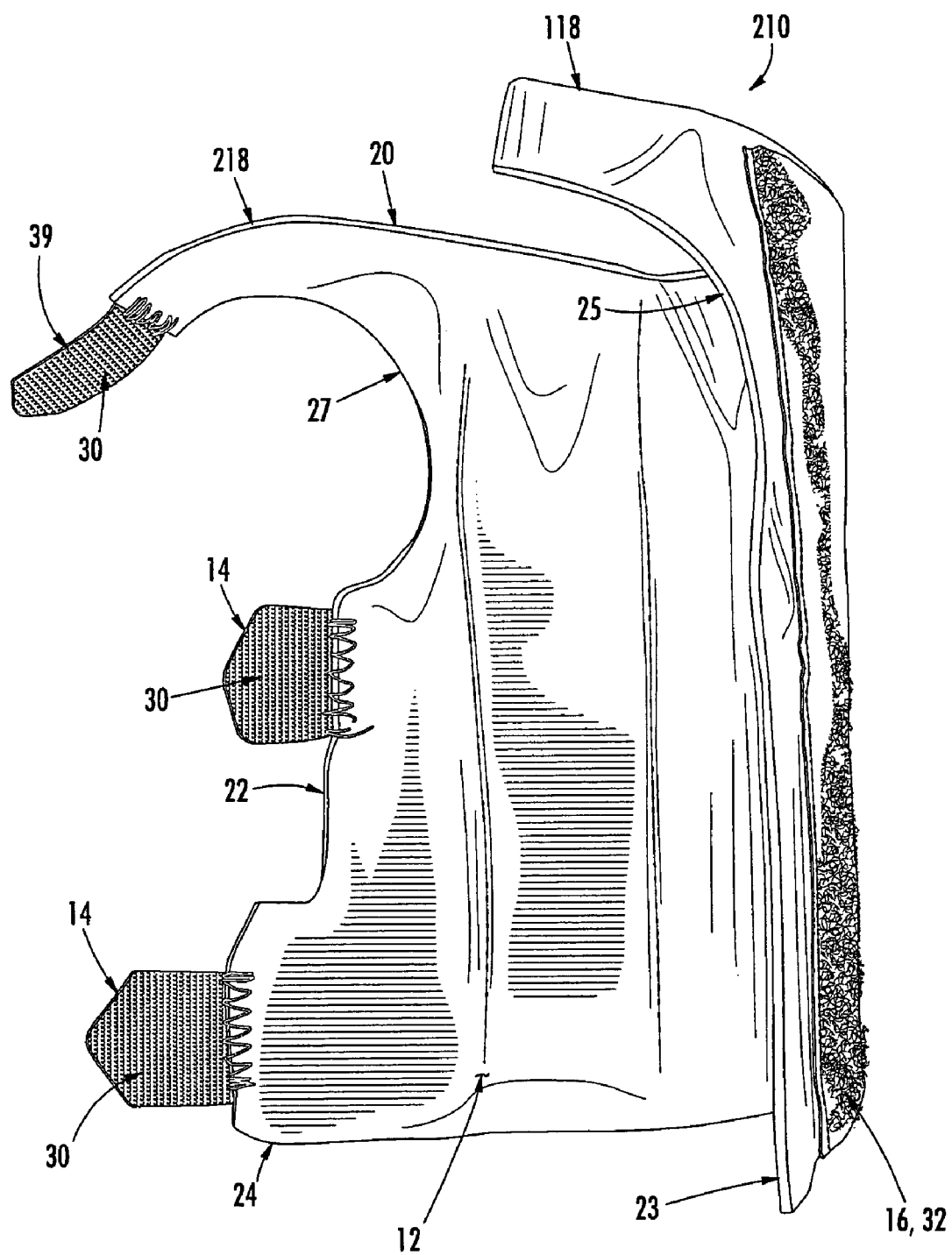
FIG. 16 is a perspective view of a wrist brace of another embodiment of the present invention.
Figure 17:
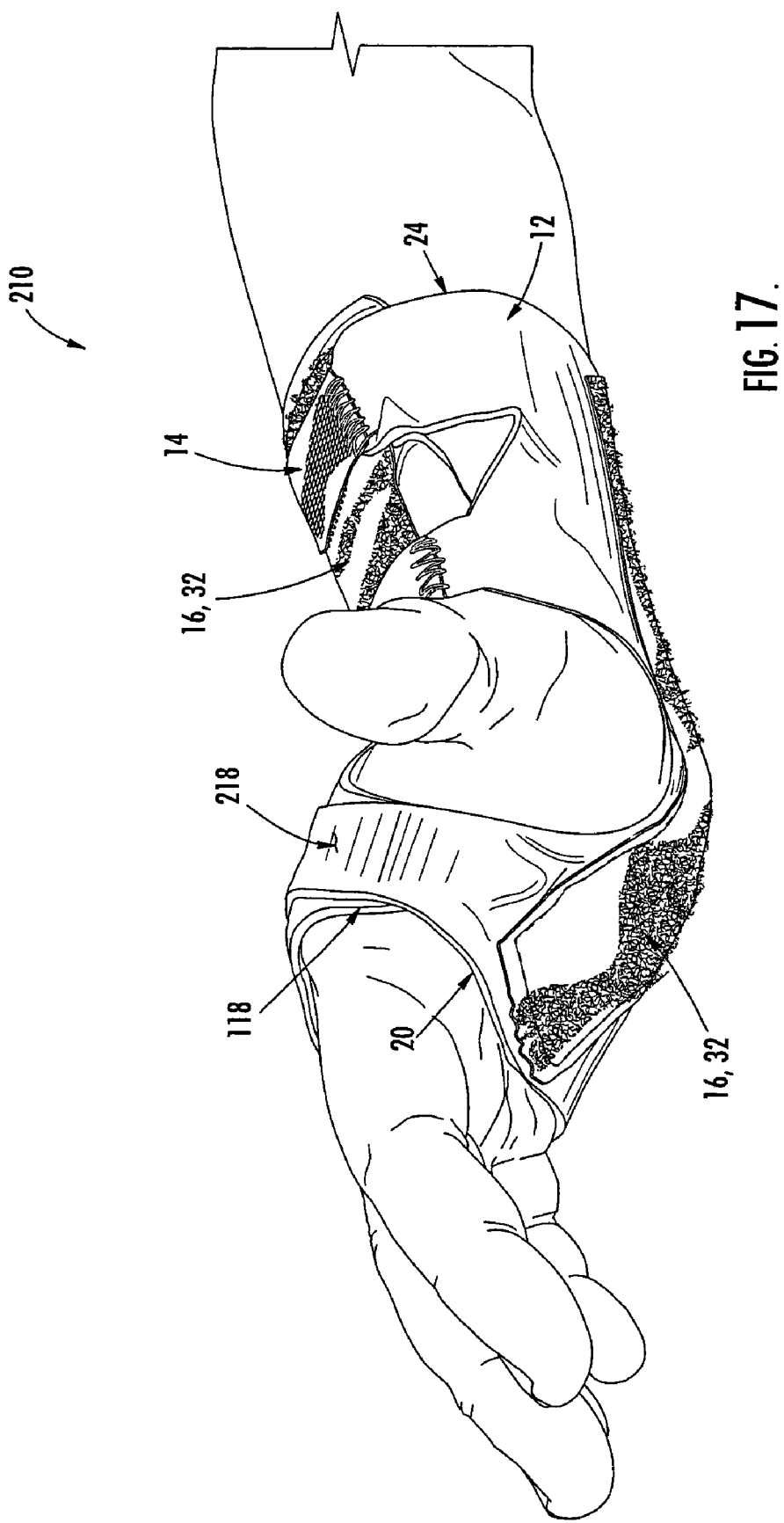
FIG. 17 is another perspective view of the wrist brace shown in FIG. 16 on a right hand.

In another embodiment, the thumb strap 118 is not attached to the sheet of material 12, such that the thumb straps 118, 218 extend from the sheet of material but have free ends, as shown in FIG. 16. The thumb strap 118 does not have a fastener on its free end such that it underlies the thumb strap 218 when the thumb strap fastener 39 is attached to the sheet of material 12.

The present invention has many advantages. The thumb hole 28 allows insertion of the wearer's thumb and facilitates proper positioning before securing the sheet of material 12 the wearer's wrist. This is done by avoiding the difficulty of trying to hold the sheet of material in place while at the same time trying to overlap the lateral edges 22, 23 and fix the fasteners 14 in place. The non-circular shape of the thumb opening also promotes positioning and improved fit by having its long axis oriented in the proximal-distal direction where the base of the thumb is typically widest. The rounded triangular shape allows for a broader opening at the base of the thumb for a further improved fit.

The ability of the thumb strap 18 to be removed and reattached via the fastener 14 allows adjustment for maximum fit and comfort. Thus, the thumb strap 18 and thumb hole 28 act to position and secure the brace 10 about a wearer's wrist. The break 38 in the sheet of material 12 ensures that when the thumb strap 18 is reattached, the distal edge 20 of the sheet of material 12 is generally continuous.

The radial portions 26 of the lateral edge 23 reduce bunching between the fasteners 14 when the fasteners are attached to the sheet 12 of material. The flared base end of the fasteners 14 provide for a more secure attachment of the fasteners to the sheet of material 12.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A wrist brace comprising:
    a sheet of flexible material having a distal edge configured to extend at least partially around a hand of a wearer, a proximal edge configured to extend at least partially around a forearm of a wearer, and a pair of opposing lateral edges configured to at least partially overlap each other so that the sheet of material extends around the wrist of the wearer, wherein the distal edge extends between the lateral edges;
    at least one lateral edge fastener attached at one end to the sheet of material and configured to extend over one of the lateral edges and attach at another end to the sheet of flexible material so as to secure the sheet of material about the wrist;

a thumb opening defined within the sheet of flexible material between the lateral edges and having a distal thumb opening edge proximate the distal edge; and a break defined in the sheet of flexible material and extending within the sheet of material from the distal edge towards the proximal edge to the thumb opening, wherein the break, the distal edge, and the distal thumb opening edge define a thumb strap, said thumb strap having a thumb strap fastener and being configured to extend between a thumb and an index finger of the wearer, and over the break, to attach to the sheet of material via the thumb strap fastener so as to enclose the thumb of the wearer within the thumb opening.

2. A wrist brace of claim 1, further comprising another lateral edge fastener configured to extend over said lateral edge, wherein the lateral edge defines a radial portion extending inwardly between said fasteners.

3. A wrist brace of claim 2, wherein said radial portions have a radius of approximately one-half of an inch.

4. A wrist brace of claim 1, wherein said thumb opening has a non-circular shape.

5. A wrist brace of claim 4, wherein the thumb opening is generally elliptical in shape.

6. A wrist brace of claim 5, wherein a major axis of the generally elliptical shape extends in a proximal-distal direction.

7. A wrist brace of claim 1, wherein the thumb opening has a generally triangular shape.

8. A wrist brace of claim 7, wherein the generally triangular shape includes a base and an apex, wherein the base extends distally and the apex extends proximally.

9. A wrist brace of claim 8, wherein said thumb opening has a length of approximately 2¾ inches from its apex to its base and a length of about 1¼ inches along its base.

10. A wrist brace of claim 1, wherein said distal edge is generally parallel to said distal thumb opening edge.

11. A wrist brace of claim 10, wherein both the distal edge of the sheet of material and the distal edge of the thumb opening arc distally.

12. A wrist brace of claim 1, wherein said distal edge defines a continuous edge extending between said lateral edges when the thumb strap fastener is attached to said sheet of flexible material.

13. A wrist brace of claim 1, wherein said lateral edge fastener has a rounded free end.

14. A wrist brace of claim 13, wherein the lateral edge fastener has a flared end secured to said sheet of material.

15. A wrist brace of claim 1, wherein each of said fasteners includes a fastening element and said sheet of flexible material supports at least one complementary fastening element configured to allow attachment of the fastening elements.

16. A wrist brace of claim 15, further comprising two elongated patches of material attached to said sheet of flexible material and supporting said complementary fastening element, said elongated patches of material extending from said proximal edge to said distal edge of said sheet of material and defining pockets sized to receive a splint.

17. A wrist brace of claim 16, wherein the thumb opening is defined by the sheet of flexible material between the elongated patches of material.

18. A wrist brace of claim 16, wherein said fastening element on the lateral edge fastener and the fastening element on the fastener of the thumb strap attach to the same elongated patch of material.

19. A wrist brace of claim 16, wherein said fastening element on the lateral edge fastener and the fastening element on the fastener of the thumb strap attach to different elongated patches of material.

20. A wrist brace comprising:

a sheet of flexible material having a distal edge configured to extend at least partially around a hand of a wearer, a proximal edge configured to extend at least partially around a forearm of a wearer, and a pair of opposing lateral edges configured to at least partially overlap each other so that the sheet of material extends around the wrist of the wearer, wherein the distal edge extends between the pair of opposing lateral edges;

at least one lateral edge fastener attached at one end to the sheet of material and configured to extend over one of the lateral edges and attach at another end to the sheet of flexible material so as to secure the sheet of material about the wrist;

a thumb opening defined within the sheet of flexible material between the distal, proximal, and lateral edges and having a distal thumb opening edge proximate the distal edge, the thumb opening having a generally triangular shape, wherein said generally triangular shape includes a base and an apex, wherein the base extends distally and the apex extends proximally; and a break defined by excising one edge of the base between the distal edge and the distal thumb opening edge, wherein the break, the distal edge, and the distal thumb opening edge define a thumb strap.

21. A wrist brace of claim 20, further comprising a plurality of undulations defined along one of the lateral edges, wherein the lateral fastener attaches at a peak of one of the undulations.

22. A wrist brace of claim 21, further comprising another lateral edge fastener attached to an adjacent peak of said undulations so that a radial portion extends inwardly between said fasteners.

23. A wrist brace of claim 21, wherein said undulations have a radius of approximately one-half of an inch.

24. A wrist brace of claim 20, wherein said thumb opening has a length of approximately 2¾ inches from its apex to its base and a length of about 1¼ inches along its base.

25. A wrist brace of claim 20, wherein said distal edge is generally parallel to said distal thumb opening edge.

26. A wrist brace of claim 25, wherein both the distal edge of the sheet of material and the distal edge of the thumb opening arc distally.

27. A wrist brace of claim 20, wherein said lateral edge fastener has a rounded free end.

28. A wrist brace of claim 27, wherein the lateral edge fastener has a flared end secured to said sheet of material.

29. A wrist brace of claim 20, wherein each of said fasteners includes a fastening element and said sheet of flexible material supports at least one complementary fastening element configured to allow attachment of the fastening elements.

30. A wrist brace of claim 29, further comprising two elongated patches of material attached to said sheet of flexible material and supporting said complementary fastening element, said elongated patches of material extending from said proximal edge to said distal edge of said sheet of material and defining pockets sized to receive a splint.

31. A wrist brace of claim 30, wherein the thumb opening is defined by the sheet of flexible material between the elongated patches of material.

32. A method of positioning a wrist brace on a hand of a wearer, said method comprising:
   extending a thumb strap over a break defined in a sheet of flexible material of the wrist brace, said break extending within the sheet of flexible material from a distal edge of the sheet of flexible material towards the proximal edge to a thumb opening defined by the sheet of flexible material adjacent the distal edge, wherein the distal edge extends between a first lateral edge and a second lateral edge;
   attaching a fastener of the thumb strap to the sheet of flexible material;
   positioning the thumb strap between a thumb and index finger of the wearer so that the thumb extends through the thumb opening;
   extending a proximal edge of the sheet of flexible material at least partially around a forearm of the wearer;
   extending the distal edge of the sheet of flexible material at least partially over the hand of the wearer;
   extending the first lateral edge of the sheet of flexible material over the second lateral edge of the sheet of flexible material so that the sheet of flexible material extends around the wrist; and
   extending at least one fastener attached to the sheet of material at one end, over the first lateral edge and attaching another end of the fastener to the sheet of flexible material so as to secure the wrist brace about the wrist.

33. A method of claim 32, wherein positioning the thumb strap includes orienting a long axis of the thumb opening in a proximal-distal direction at a base of the thumb.

34. A method of claim 32, wherein attaching the thumb strap includes closing the break extending between the distal edge and thumb opening so that the distal edge extends continuously around the hand of the wearer.

* * * * *

UNITED STATES PATENT AND TRADEMARK OFFICE
CERTIFICATE OF CORRECTION

PATENT NO. : 7,364,556 B2 Page 1 of 1
APPLICATION NO. : 10/701137
DATED : April 29, 2008
INVENTOR(S) : Weaver, II It is certified that error appears in the above-identified patent and that said Letters Patent is hereby corrected as shown below:

Column 3,

Line 11, "are" should read --arc--.

Signed and Sealed this

Fifth Day of August, 2008

JON W. DUDAS
*Director of the United States Patent and Trademark Office*